US008727994B2

(12) United States Patent
Kim et al.

(10) Patent No.: US 8,727,994 B2
(45) Date of Patent: May 20, 2014

(54) CELL AND CHANNEL OF ULTRASONIC TRANSDUCER, AND ULTRASONIC TRANSDUCER INCLUDING THE SAME

(75) Inventors: Dong-kyun Kim, Suwon-si (KR); Hyung-jae Shin, Seongnam-si (KR); Seok-whan Chung, Suwon-si (KR); Byung-gil Jeong, Anyang-si (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 213 days.

(21) Appl. No.: 13/168,473

(22) Filed: Jun. 24, 2011

(65) Prior Publication Data

US 2012/0150041 A1 Jun. 14, 2012

(30) Foreign Application Priority Data

Dec. 14, 2010 (KR) ........................ 10-2010-0127871

(51) Int. Cl.

| | |
|---|---|
| *A61B 8/14* | (2006.01) |
| *A61B 8/00* | (2006.01) |
| *B06B 1/02* | (2006.01) |
| *B06B 3/00* | (2006.01) |
| *H01L 41/00* | (2013.01) |
| *G01S 15/89* | (2006.01) |

(52) U.S. Cl.
CPC ... *A61B 8/44* (2013.01); *A61B 8/14* (2013.01); *B06B 1/0292* (2013.01); *B06B 1/02* (2013.01); *B06B 3/00* (2013.01); *H01L 41/00* (2013.01); *G01S 15/8906* (2013.01)
USPC ............ 600/459; 600/437; 310/309; 310/311

(58) Field of Classification Search
None
See application file for complete search history.

(56) References Cited

U.S. PATENT DOCUMENTS

| | | | | |
|---|---|---|---|---|
| 7,027,284 | B2 * | 4/2006 | Kobayashi et al. | 361/278 |
| 7,615,834 | B2 | 11/2009 | Khuri-Yakub et al. | |
| 7,618,391 | B2 * | 11/2009 | Madsen et al. | 604/9 |
| 2002/0079743 | A1 * | 6/2002 | Ma et al. | 307/109 |
| 2004/0085858 | A1 * | 5/2004 | Khuri-Yakub et al. | 367/181 |
| 2005/0046311 | A1 * | 3/2005 | Baumgartner et al. | 310/334 |
| 2005/0096546 | A1 * | 5/2005 | Hazard et al. | 600/447 |
| 2005/0146240 | A1 * | 7/2005 | Smith et al. | 310/309 |
| 2005/0177045 | A1 * | 8/2005 | Degertekin et al. | 600/457 |
| 2005/0200241 | A1 | 9/2005 | Degertekin | |

(Continued)

FOREIGN PATENT DOCUMENTS

| | | | |
|---|---|---|---|
| JP | 2004350700 | A | 12/2004 |
| JP | 2007-214874 | A | 8/2007 |

(Continued)

OTHER PUBLICATIONS

Communication, dated Nov. 14, 2013, issued by the U.S. Patent and Trademark Office in counterpart U.S. Appl. No. 13/568,827.

*Primary Examiner* — Long V. Le
*Assistant Examiner* — Bradley Impink
(74) *Attorney, Agent, or Firm* — Sughrue Mion, PLLC

(57) ABSTRACT

A cell of an ultrasonic transducer is provided. The cell includes a substrate; a supporting portion disposed on the substrate; a thin film spaced apart from the substrate and the supporting portion; and a connection portion which connects the supporting portion and the thin film. The connection portion may include a deformation portion that is elastically deformable. A channel of the ultrasonic transducer includes a plurality of cells arranged in an array. The ultrasonic transducer includes a plurality of channels arranged in an array.

25 Claims, 9 Drawing Sheets

(56) References Cited

U.S. PATENT DOCUMENTS

| | | |
|---|---|---|
| 2005/0200541 A1* | 9/2005 | Bassily .................. 343/755 |
| 2006/0272139 A1* | 12/2006 | Kinoshita ................ 29/25.35 |
| 2007/0299345 A1 | 12/2007 | Adachi et al. |
| 2008/0194053 A1 | 8/2008 | Huang |
| 2008/0197751 A1* | 8/2008 | Huang .................... 310/311 |
| 2009/0076393 A1* | 3/2009 | Adachi et al. ............ 600/459 |
| 2010/0232257 A1* | 9/2010 | Tanaka et al. ............... 367/7 |
| 2011/0128083 A1* | 6/2011 | Pomarico et al. ......... 331/156 |
| 2012/0150041 A1 | 6/2012 | Kim et al. |

FOREIGN PATENT DOCUMENTS

| | | |
|---|---|---|
| JP | 2007-274293 A | 10/2007 |
| JP | 2009-100459 A | 5/2009 |
| JP | 2009-118093 A | 5/2009 |
| JP | 2009182838 A | 8/2009 |
| WO | 2005/077012 A2 | 8/2005 |
| WO | 2007/005036 A2 | 1/2007 |
| WO | 2008/038454 A1 | 4/2008 |

* cited by examiner

CELL AND CHANNEL OF ULTRASONIC TRANSDUCER, AND ULTRASONIC TRANSDUCER INCLUDING THE SAME

CROSS-REFERENCE TO RELATED APPLICATION

This application claims priority from Korean Patent Application No. 10-2010-0127871, filed on Dec. 14, 2010, in the Korean Intellectual Property Office, the disclosure of which is incorporated herein in its entirety by reference.

BACKGROUND

1. Field

Apparatuses consistent with the present disclosure relate to a cell and a channel of an ultrasonic transducer, and the ultrasonic transducer including the same.

2. Description of the Related Art

Micromachined ultrasonic transducers (MUTs) are apparatuses that convert an electrical signal into an ultrasonic signal or convert an ultrasonic signal into an electrical signal. Ultrasonic transducers are used in, for example, medical image diagnosis apparatuses, and may obtain photos and images of body tissues or body organs non-invasively. An ultrasonic transducer may include a piezoelectric micromachined ultrasonic transducer (pMUT), a capacitive micromachined ultrasonic transducer (cMUT), a magnetic micromachined ultrasonic transducer (mMUT), or the like, according to its transduction method.

SUMMARY

One or more embodiments provide a cell and a channel of an ultrasonic transducer, and the ultrasonic transducer including the same.

According to an aspect of an exemplary embodiment, a cell of an ultrasonic transducer includes: a substrate; a supporting portion disposed on the substrate; a thin film spaced apart from the substrate and the supporting portion; and a connection portion which connects the supporting portion and the thin film.

The connection portion may include a support contact portion connected to the supporting portion, a thin film contact portion connected to the thin film, and a deformation portion which connects the support contact portion and the thin film contact portion and which is elastically deformable.

An elastic deformation of the deformation portion causes the thin film to vibrate.

The cell may further include a first electrode disposed on the substrate.

The cell may further include an insulating layer disposed on the first electrode.

The cell may further include a second electrode disposed on the thin film.

The cell may further include a feeder which is disposed on the connection portion and which is electrically connected to the second electrode.

The thin film may be a conductive thin film.

The cell may further include a piezoelectric layer disposed on the connection portion.

The cell may further a first electrode disposed under the piezoelectric layer and a second electrode disposed on the piezoelectric layer.

The cell may include a cavity defined by the substrate, the supporting portion, the thin film, and the connection portion.

According to an aspect of another exemplary embodiment, a channel of an ultrasonic transducer includes a plurality of cells, wherein the cells are arranged in an m×n array, wherein m and n are natural numbers greater than 1.

According to an aspect of another exemplary embodiment, a channel of an ultrasonic transducer includes a substrate including a plurality of recesses and supporting portions; a plurality of thin films spaced apart from the recesses; and a plurality of connection portions, wherein each of the connection portions connects one of the thin films and a supporting portion.

The connection portion may include a support contact portion connected to the supporting portion, a thin film contact portion connected to the thin film, and a deformation portion which connects the support contact portion and the thin film contact portion and which is elastically deformable.

An elastic deformation of the deformation portion may cause the thin film to vibrate in a direction perpendicular to the substrate.

The channel may further include a first electrode disposed in each of the recesses.

The channel may further include an insulating layer disposed on each of the first electrodes.

The channel may further include a second electrode disposed on each of the thin films.

The channel may further include a feeder disposed on each of the connection portions and which is electrically connected to the second electrode.

The thin film may be a conductive thin film.

The channel may further include a piezoelectric layer disposed on each of the connection portions.

The channel may further include a first electrode disposed under the piezoelectric layer and a second electrode disposed on the piezoelectric layer.

A cavity may be defined by the substrate, one of the supporting portions, one of the plurality of thin films, and one of the plurality of connection portions.

According to an aspect of another exemplary embodiment, an ultrasonic transducer includes a plurality of the channels, wherein the channels are arranged in an m×n array, where m and n are natural numbers greater than 1.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1A:
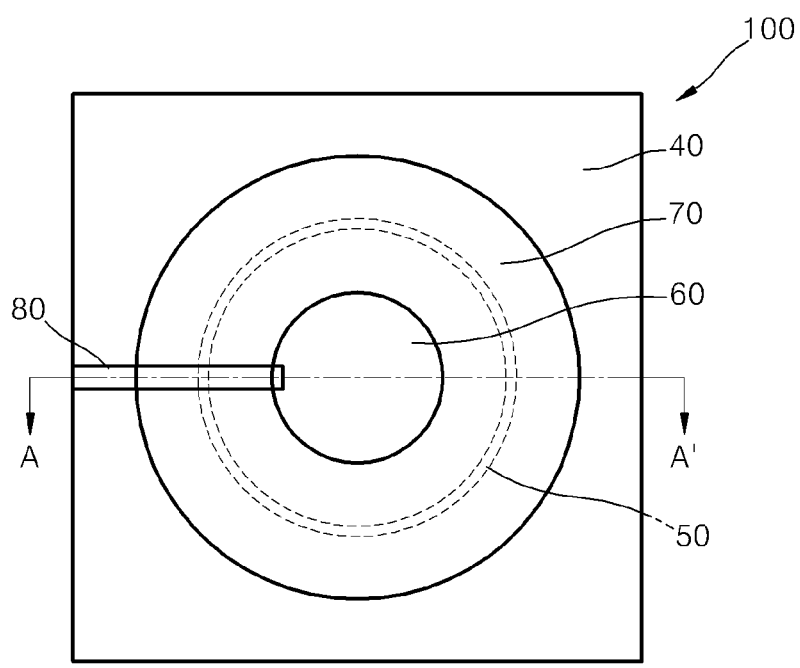
FIG. 1A is a schematic plane view illustrating a cell of an ultrasonic transducer, according to an exemplary embodiment of the present invention.

Various exemplary embodiments will now be described more fully with reference to the accompanying drawings.

Detailed illustrative exemplary embodiments are disclosed herein. However, specific structural and functional details disclosed herein are merely representative for purposes of describing exemplary embodiments. This invention may, however, may be embodied in many alternate forms and should not be construed as limited to only the exemplary embodiments set forth herein.

Like numbers refer to like elements throughout the description of the figures.

It will be understood that, although the terms 'first', 'second', etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items.

It will be understood that when an element or layer is referred to as being "formed on," another element or layer, it can be directly or indirectly formed on the other element or layer. That is, for example, intervening elements or layers may be present. In contrast, when an element or layer is referred to as being "directly formed on," to another element, there are no intervening elements or layers present. Other words used to describe the relationship between elements or layers should be interpreted in a like fashion (e.g., "between," versus "directly between," "adjacent," versus "directly adjacent," etc.).

The terminology used herein is for the purpose of describing particular embodiments only and is not intended to be limiting of exemplary embodiments. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

In the drawings, the thicknesses of layers and regions are exaggerated for clarity.

Figure 1B:
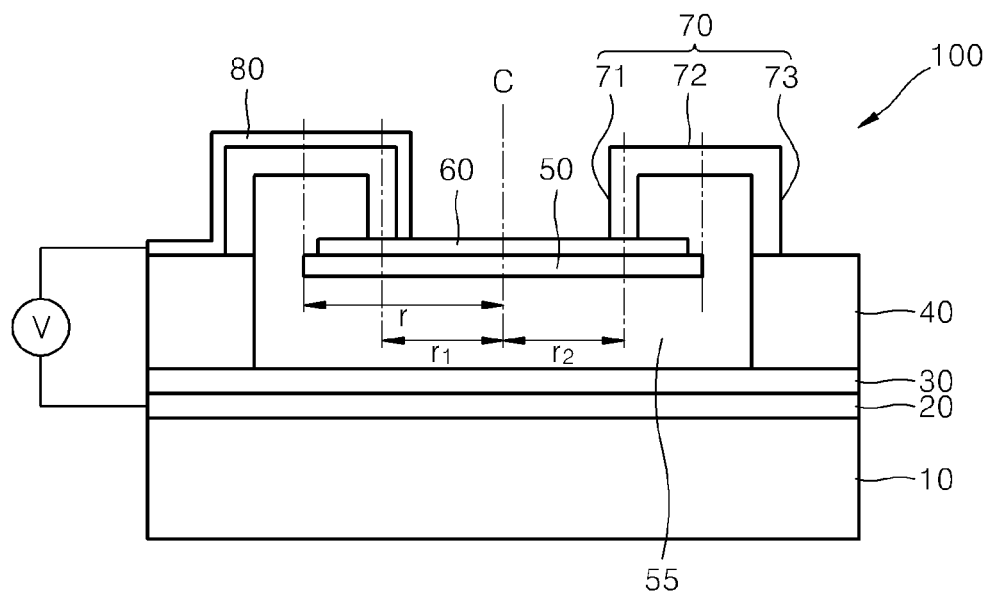
FIG. 1B is a schematic cross-sectional view illustrating the cell of the ultrasonic transducer of FIG. 1A.
Figure 1C:
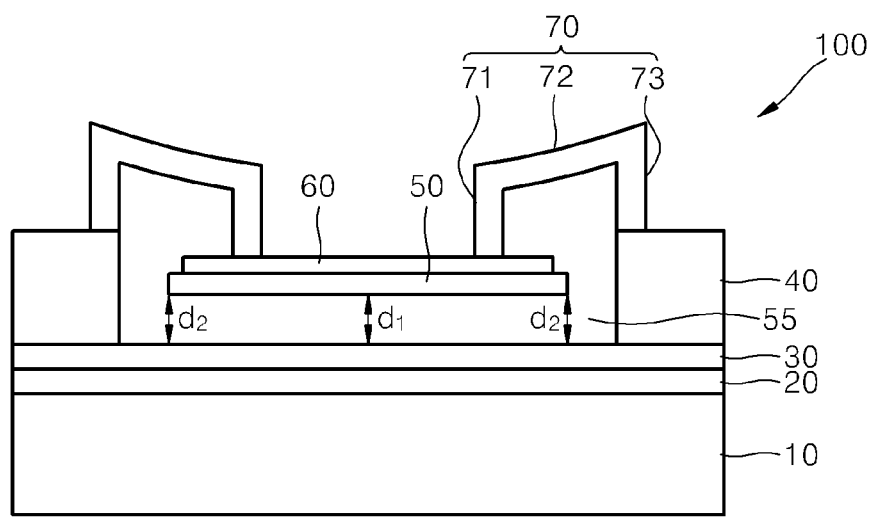
FIG. 1C is a schematic cross-sectional view illustrating the cell of the ultrasonic transducer of FIG. 1A.

FIG. 1A is a schematic plane view illustrating a cell 100 of an ultrasonic transducer, according to an exemplary embodiment. FIG. 1B is a schematic cross-sectional view illustrating the cell 100 of the ultrasonic transducer of FIG. 1A. FIG. 1C illustrates the cell 100 including a thin film 50 that vibrates.

Figure 9:
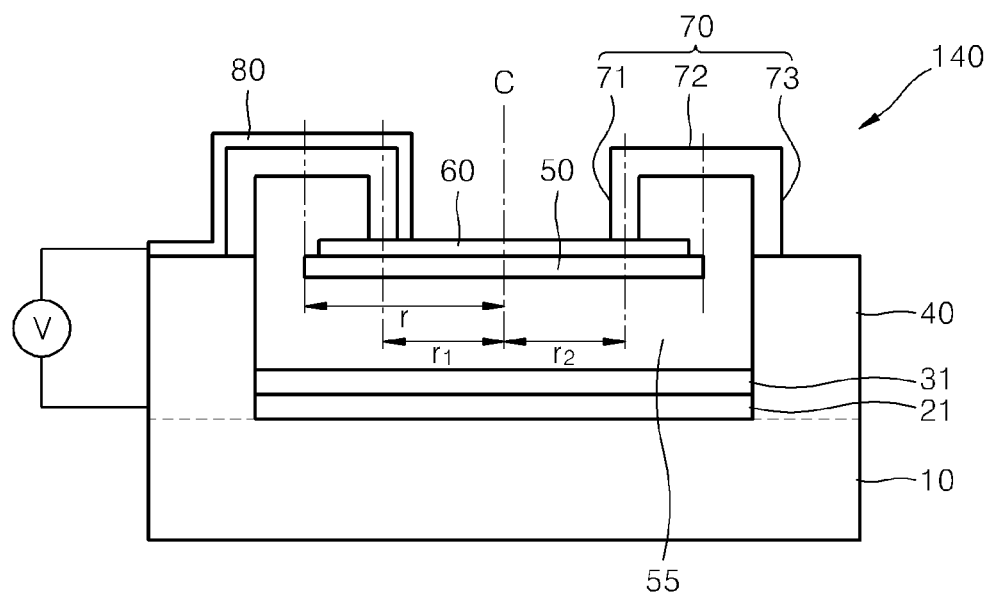
FIG. 9 is a schematic cross-sectional view illustrating a cell of an ultrasonic transducer, according to an exemplary embodiment.

Referring to FIGS. 1A and 1B, the cell 100 may include substrate 10, a supporting portion 40 disposed on the substrate 10, the thin film 50 spaced apart from the substrate 10 and the supporting portion 40, and a connection portion 70 for connecting the supporting portion 40 and the thin film 50. As shown in FIG. 9, the supporting portion 40 may be disposed directly on the substrate 10 or may be integrally formed with the substrate 10. The cell 100 of the ultrasonic transducer may further include a first electrode 20 that is disposed on the substrate 10, an insulating layer 30 that is disposed on the first electrode 20, a second electrode 60 disposed on the thin film 50, and a feeder 80 that is connected to the second electrode 60. The cell 100 may be a cell of a cMUT. That is, the first electrode 20 and the second electrode 60 may form a capacitor.

The substrate 10 may be formed of a material such as silicon (Si) or glass. The substrate 10 may be a silicon on insulator (SOI) wafer, or the like. The supporting portion 40 may be disposed on the substrate 10, and the supporting portion 40 may be integrally formed with the substrate 10. For example, the supporting portion 40 may be formed on the substrate 10 by etching the substrate 10.

The first electrode 20 may be formed on the substrate 10 and may be disposed on an area on the substrate 10 corresponding to the location of the thin film 50 or the second electrode 60. The first electrode 20 may be formed of a conductive material, for example, Cu, Al, Au, Cr, Mo, Ti, Pt, or the like.

The insulating layer 30 may be disposed on the first electrode 20, and may electrically insulate the first electrode 20 and the second electrode 60 from each other. Also, when the thin film 50 is formed of a conductive material, the insulating layer 30 may insulate the first electrode 20 and the conductive thin film 50 from each other.

The thin film 50 may be spaced apart from the substrate 10 and the supporting portion 40. That is, the thin film 50 may be disposed in a recess 41 (see FIG. 8B) formed by the substrate 10 and the supporting portion 40 so as to be spaced apart from the substrate 10 and the supporting portion 40. The thin film 50 may be formed of, for example, Si, silicon-nitride ($Si_xN_y$), parylene, or the like. The thin film 50 may have a circular shape or a polygonal shape, but is not limited thereto. In addition, the thin film 50, the substrate 10, the supporting portion 40, and the connection portion 70 may define a cavity 55, which may be in a vacuum state.

The connection portion 70 may connect the supporting portion 40 and the thin film 50, and may be formed of, for example, Si, $Si_xN_y$, parylene, or the like. The connection portion 70 may have the shape of a tube cut in half in the horizontal direction, and a cross-section of the connection portion 70 may be bridge-shaped. The connection portion 70 includes a thin film contact portion 71, a support contact portion 73, and a deformation portion 72.

The thin film contact portion 71 may be connected to an upper surface of the thin film 50 and may extend upward from the thin film 50 in a direction perpendicular to the thin film 50. The thin film contact portion 71 may be symmetrically disposed about the center C of the thin film 50. That is, as shown in FIG. 1B, a distance $r_1$ between one thin film contact portion 71 and the center C of the thin film 50 may be equal to a distance $r_2$ between the other thin film contact portion 71 and the center C of the thin film 50. The distances $r_1$ and $r_2$ may be equal to or less than a radius r of the thin film 50, for example, may be a half of the radius r of the thin film 50 ($r_1=r_2=0.5r$). As shown in FIG. 1A, the thin film may surround a circumference of the thin film 50, so the thin film contact portion may form a circular wall extending upward from the thin film 50. If the second electrode 60 is formed on the upper surface of the thin film 50, the thin film contact portion 71 may be connected to an upper surface of the second electrode 60, rather than to the thin film directly. The support contact portion 73 is connected to an upper surface of the supporting portion 40, and may extend in a direction perpendicular to the supporting portion 40.

The deformation portion 72 is disposed between the thin film contact portion 71 and the support contact portion 73 and is elastically deformable. The deformation portion 72 connects the thin film contact portion 71 and the support contact portion 73, and may be parallel to the substrate 10 or the thin film 50 when in a neutral position as shown in FIG. 1B. In addition, the deformation portion 72 may be formed of an elastic material or may be elastically deformable due to its thinness. The thin film 50 may vibrate in a direction perpendicular to the substrate 10 due to the elastic deformation of the deformation portion 72. That is, the thin film 50 may move in a vertical direction, like a piston, with respect to the substrate 10. Accordingly, in the cell 100 of the ultrasonic transducer, an average electrostatic force between the first electrode 20 and the second electrode 60 and an amount of change in the volume of the cavity 55 due to the vibration of the thin film 50 may be increased, as compared to that in a related art ultrasonic transducer. The increase in the average electrostatic force and the amount of change in the volume of the cavity 55 may improve the transmission output and the reception sensitivity of the cell 100 of the ultrasonic transducer.

The second electrode 60 may be disposed on the upper surface of the thin film 50 or on the lower surface of the thin film 50. The second electrode 60 may be formed of a conductive material, for example, Cu, Al, Au, Cr, Mo, Ti, Pt, or the like. The feeder 80 may be disposed on the supporting portion 40 and the connection portion 70, and may extend to the second electrode 60. The feeder 80 transmits an electrical signal from an external power source V to the second electrode 60. Also, the feeder 80 may transmit a variation in the electrical signal between the first and second electrodes 20 and 60 to an external element, for example, may transmit a variation in the electrical signal due to a change in the capacitance. According to this embodiment, the external power source V may generate a direct current (DC) voltage or an alternating current (AC) voltage. The thin film 50 may be formed of a conductive material such as a doped Si, and the second electrode 60 may be omitted. In this case, the first electrode 20 and the conductive thin film 50 may form a capacitor, and the feeder 80 may transmit an electrical signal to the conductive thin film 50 or may transmit a variation in the electrical signal due to a change in the capacitance between the first electrode 20 and the conductive thin film 50.

Next, referring to FIG. 1C, an operation of the cell 100 of the ultrasonic transducer will be described. First, an operation of the transmission properties of the cell 100 will be described. When a DC voltage (not shown) is applied to the first and second electrodes 20 and 60, the thin film 50 may be disposed in a neutral position in which an electrostatic force between the first and second electrodes 20 and 60 is balanced by the force of gravity on the thin film 50. When the DC voltage (not shown) is applied to the first and second electrodes 20 and 60, and an AC voltage is also applied to the first and second electrodes 20 and 60, the thin film 50 vibrates due to the resultant variation in the electrostatic force between the first and second electrodes 20 and 60. The thin film 50 of the cell 100 of the ultrasonic transducer does not vibrate due to the elastic deformation of the thin film 50 alone, but vibrates due to the deformation of the deformation portion 72. Since an edge of the thin film 50 is not directly fixed to the supporting portion 40, the degree of freedom of the movement of the thin film 50 increases as compared to a cell in which edges of a thin film are directly fixed to the supporting portion 40. Accordingly, the thin film 50 does not arch, but rather moves in a direction perpendicular to the substrate 10 so as to be remain parallel to the substrate 10 during vibration. That is, the thin film 50 may move in a vertical direction, like a piston, with respect to the substrate 10. Accordingly, the amount of change in the volume of the cavity 55 of the cell 100 may be increased as compared with a transducer in which the thin film is directly attached to the supporting portion 40.

In the cell 100 of the ultrasonic transducer according to this embodiment, when the thin film 50 vibrates, a distance $d_1$ between a center of the thin film 50 and the insulating layer 30 may remain equal to a distance $d_2$ between an outer portion of the thin film 50 and the insulating layer 30. Accordingly, an electrostatic force between centers of the first and second electrodes 20 and 60 may remain equal to an electrostatic force between outer portions of the first and second electrodes 20 and 60. That is, the electrostatic force between the first and second electrodes 20 and 60, may be uniformly distributed. Accordingly, an average electrostatic force between the first and second electrodes 20 and 60 may be increased as compared to a cell in which the thin film is directly attached to the supporting portion, and therefore does not remain parallel to the substrate when vibrating. Thus, the amount of change in the volume of the cavity 55 of the cell 100 of the ultrasonic transducer according to the present embodiment and the average electrostatic force between the first and second electrodes 20 and 60 are increased, thereby improving the transmission output of the cell 100 of the ultrasonic transducer.

An operation of the reception properties of the cell 100 of the ultrasonic transducer according to the present embodiment is as follows. Similarly to the function of the cell 100 during transmission, during reception, when a DC voltage (not shown) is applied to the first and second electrodes 20 and 60, the thin film 50 may be disposed in a neutral position in which the electrostatic force between the first and second electrodes 20 and 60 is balanced by the force of gravity on the thin film 50. When the DC voltage (not shown) is being applied to the first and second electrodes 20 and 60, and a physical signal, e.g., ultrasonic waves, is applied to the thin film 50 from an external source, a resultant movement of the thin film 50 causes the electrostatic force between the first and second electrodes 20 and 60 to change. The cell 100 may receive ultrasonic waves from the outside, and the ultrasonic waves may be sensed based on the change in the electrostatic force. As discussed above with respect to the function of the cell 100 during transmission, during reception, the thin film 50 of the cell 100 may move in a direction perpendicular to the substrate 10 so as to remain parallel to the substrate 10. Thus, an amount of change in the volume of the cavity 55 of the cell 100 and the average electrostatic force between the first and second electrodes 20 and 60 are increased, thereby increasing the reception sensitivity of the cell 100 of the ultrasonic transducer.

Figure 2A:
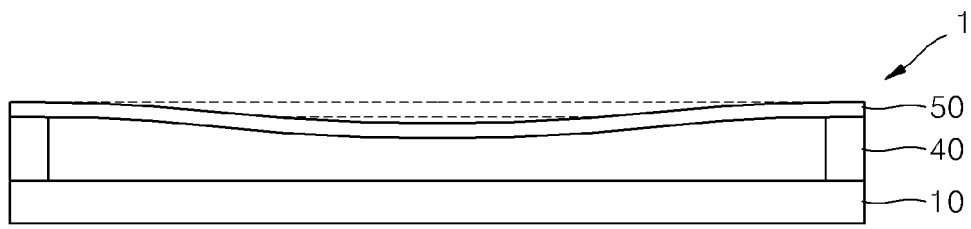
FIGS. 2A and 2B are schematic cross-sectional views each illustrating a cell of an ultrasonic transducer, according to a comparative example.
Figure 2B:
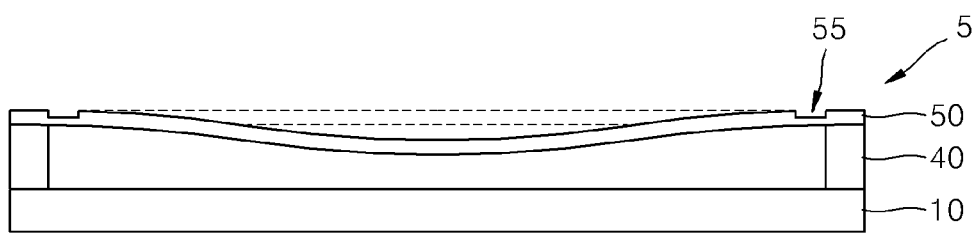
Figure 2C:
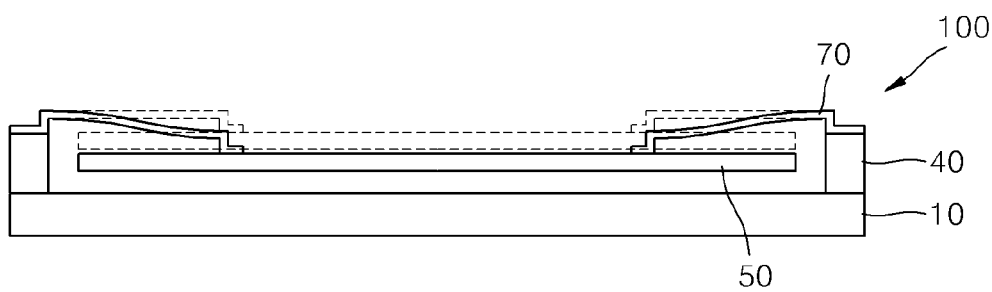
FIG. 2C is a schematic cross-sectional view illustrating the cell of the ultrasonic transducer of FIG. 1A.

FIGS. 2A and 2B schematically illustrate respective cross-sections of cells 1 and 5 of ultrasonic transducers, according to comparative examples. FIG. 2C schematically illustrates a cross-section of a cell 100 of an ultrasonic transducer according to an exemplary embodiment. The thickness of the thin film 50 in each of FIGS. 2A, 2B, and 2C is the same, and the thickness of the portion of the thin film under the trench 55 in FIG. 2B is half the thickness of the thin film 50 in other regions of the cell 5 of FIG. 2B. The thickness of the connection portion 70 of the cell 100 in FIG. 2C is half the thickness of the thin film 50.

Referring to FIG. 2A, in the cell 1 of the ultrasonic transducer according to the comparative example of FIG. 2A, an edge of the thin film 50 is fixed to a supporting portion 40, and thus the cell 1 has a clamped shape. Referring to FIG. 2B, in the cell 5 of the ultrasonic transducer according to the comparative example of FIG. 2B, an edge of the thin film 50 is also fixed to a supporting portion 40, and thus the cell 5 has a clamped shape. The cell 5 of FIG. 2B also includes a trench 55 formed at the edge of the thin film 50. The trench 55 mitigates constraints on the movement of the thin film 50 of the cell 5 of the ultrasonic transducer. Simulations show that an amount of change in the volume of the cavity of the cell 5 of the ultrasonic transducer of FIG. 2B is increased as compared to that of the cell 1 of the ultrasonic transducer of FIG. 2A. Further, the average electrostatic force generated by the cell 5 of the ultrasonic transducer of FIG. 2B is increased as compared to that of the cell 1 of the ultrasonic transducer of FIG. 2A.

As shown in FIG. 2C, in the cell 100 of an ultrasonic transducer according to an exemplary embodiment, the thin film 50 of the cell 100 is not directly fixed to the supporting portion 40, but rather is fixed to the supporting portion 40 via the connection portion 70. Accordingly, constraints on the movement of the thin film 50 may be further mitigated as compared to that of the thin films 50 of cells 1 and 5 according to the comparative examples of FIGS. 2A and 2B. The thin film 50 of FIG. 2C may move in a vertical direction, like a piston, with respect to the substrate 10. Simulations show that in the cell 100 of the ultrasonic transducer, of FIG. 2C, the amount of change in the volume of the cavity and the average electrostatic force generated are further increased as compared to the cells 1 and 5 of the ultrasonic transducers as shown in FIGS. 2A and 2B. Accordingly, the cell 100 of the ultrasonic transducer according to an exemplary embodiment as shown in FIG. 2C may have an increased transmission output and an increased reception sensitivity as compared to the cells 1 and 5 of the ultrasonic transducers as shown in FIGS. 2A and 2B.

Figure 3:
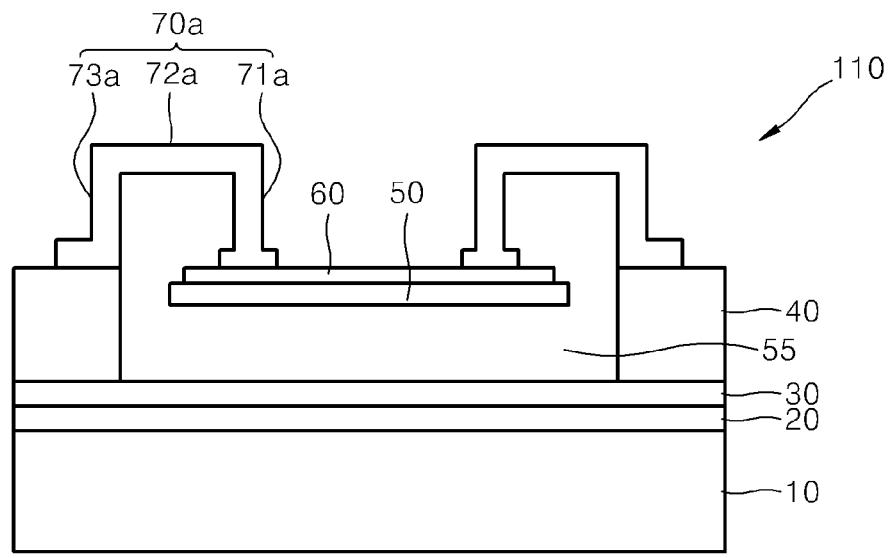
FIG. 3 is a schematic cross-sectional view illustrating a cell of an ultrasonic transducer, according to another exemplary embodiment.

FIG. 3 is a schematic cross-sectional view illustrating a cell 110 of an ultrasonic transducer, according to another exemplary embodiment. Hereinafter, differences between the cell 100 of FIG. 1B and the cell 110 of FIG. 3 will be described.

Referring to FIG. 3, the cell 110 may include a substrate 10, a supporting portion 40 disposed on the substrate 10, a thin film 50 spaced apart from the substrate 10 and the supporting portion 40, and a connection portion 70a for connecting the supporting portion 40 and the thin film 50. The cell 110 may further include a first electrode 20 disposed on the substrate 10, an insulating layer 30 disposed on the first electrode 20, and a second electrode 60 disposed on the thin film 50.

The connection portion 70a may connect the supporting portion 40 and the thin film 50, and may be formed of, for example, Si, $Si_xN_y$, parylene, or the like. The connection portion 70a may have the shape of a tube that is cut in half in a horizontal direction, and the cross-section of the connection portion 70a may be bridge-shaped. The connection portion 70a may include a thin film contact portion 71a, a support contact portion 73a, and a deformation portion 72a. The thin film contact portion 71a is connected to an upper surface of the thin film 50 or to an upper surface of the second electrode 60, and extends in a direction perpendicular to the thin film 50. Ends of the thin film contact portion 71a may be configured to increase contact areas between the ends of the thin film contact portion 71a and the thin film 50. For example, the ends of the thin film contact portion 71a may be shaped such that the ends extend bilaterally. Accordingly, the thin film 50 may be firmly coupled to the thin film contact portion 71a. The support contact portion 73a may be connected to an upper surface of the supporting portion 40, and may extend in a direction perpendicular to the supporting portion 40. Also, the support contact portion 73a may be disposed over a wide area on the upper surface of the supporting portion 40 in order to withstand the weight applied to the connection portion 70a. Accordingly, the weight applied to the connection portion 70a may be distributed over a wide area of the supporting portion 40 via the support contact portion 73a.

Figure 4:
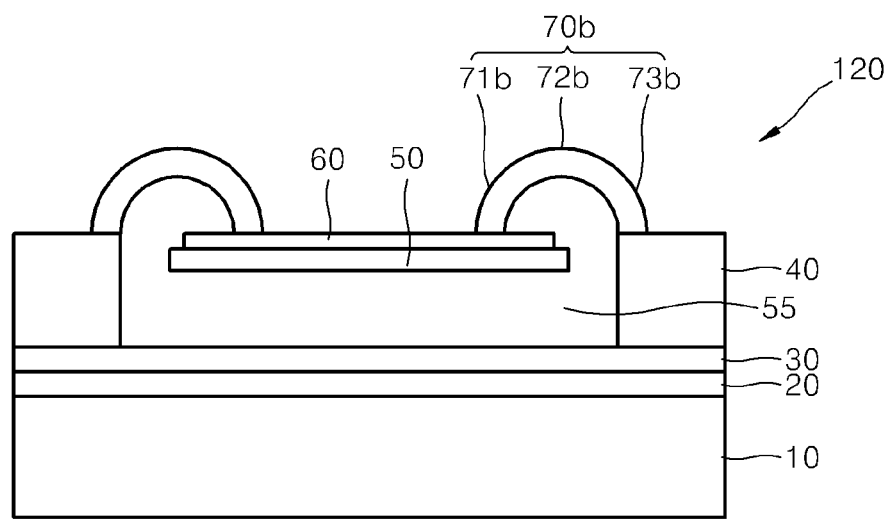
FIG. 4 is a schematic cross-sectional view illustrating a cell of an ultrasonic transducer, according to another exemplary embodiment.

FIG. 4 is a schematic cross-sectional view illustrating a cell 120 of an ultrasonic transducer, according to another exemplary embodiment. Hereinafter, differences between the cells 100 and 110 respectively of FIGS. 1B and 3 and the cell 120 of FIG. 4 will be described.

Referring to FIG. 4, the cell 120 may include a substrate 10, a supporting portion 40 disposed on the substrate 10, a thin film 50 spaced apart from the substrate 10 and the supporting portion 40, and a connection portion 70b for connecting the supporting portion 40 and the thin film 50. The cell 120 may further include a first electrode 20 disposed on the substrate 10, an insulating layer 30 disposed on the first electrode 20, and a second electrode 60 disposed on the thin film 50.

The connection portion 70b may have the shape of a tube that is cut in half in a horizontal direction, and the cross-section of the connection portion 70b be arch-shaped, as illustrated in FIG. 4. The arch-shaped connection portion 70b may include a thin film contact portion 71b, a support contact portion 73b, and a deformation portion 72b. The thin film contact portion 71b may be connected to an upper surface of the thin film 50 or to an upper surface of the second electrode 60, and may have a curved-shape. Ends of the thin film contact portion 71b may be configured to increase contact areas between the ends of the thin film contact portion 71b and the thin film 50. For example, the ends of the thin film contact portion 71b may extend bilaterally, similar to the thin film contact portion 71a of FIG. 3. Accordingly, the thin film 50 may be firmly coupled to the thin film contact portion 71b.

The support contact portion 73b may be connected to an upper surface of the supporting portion 40, and may have a curved-shape. Also, the support contact portion 73b may be disposed over a wide area on the upper surface of the supporting portion 40 in order to withstand the weight applied to the connection portion 70, similar to the support contact portion 71a of FIG. 3. Accordingly, the weight applied to the connection portion 70 may be distributed over a wide area of the supporting portion 40 via the support contact portion 73b. The deformation portion 72b may have a curved-shape connecting the thin film contact portion 71b and the support contact portion 73b, and may function as described above.

Figure 5:
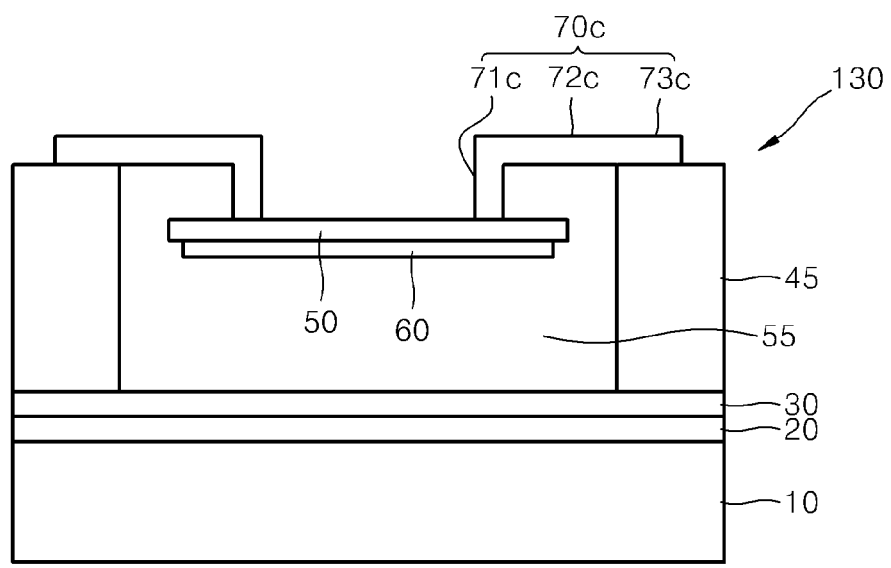
FIG. 5 is a schematic cross-sectional view illustrating a cell of an ultrasonic transducer, according to another exemplary embodiment.

FIG. 5 is a schematic cross-sectional view illustrating a cell 130 of an ultrasonic transducer, according to another exemplary embodiment. Hereinafter, differences between the cells 100, 110, and 120 respectively of FIGS. 1B, 3, and 4 and the cell 130 of FIG. 5 will be described.

Referring to FIG. 5, the cell 130 may include a substrate 10, a supporting portion 45 disposed on the substrate 10, a thin film 50 spaced apart from the substrate 10 and the supporting portion 45, and a connection portion 70c for connecting the supporting portion 45 and the thin film 50. The cell 130 may further include a first electrode 20 disposed on the substrate

10, an insulating layer 30 disposed on the first electrode 20, and a second electrode 60 disposed under the thin film 50.

The connection portion 70c may connect the supporting portion 45 and the thin film 50, and may be formed of, for example, Si, $Si_xN_y$, parylene, or the like. A cross-section of the connection portion 70c may be L-shaped, as illustrated in FIG. 5. The connection portion 70c may include a thin film contact portion 71c, a support contact portion 73c, and a deformation portion 72c. The thin film contact portion 71c may be connected to an upper surface of the thin film 50 and may extend in a direction perpendicular to the thin film 50. Ends of the thin film contact portion 71c may be configured to increase contact areas between the ends of the thin film contact portion 71c and the thin film 50. For example, the ends of the thin film contact portion 71c may extend bilaterally, similar to the thin film contact portion 71a of FIG. 3. Accordingly, the thin film 50 may be firmly coupled to the thin film contact portion 71c.

The support contact portion 73c may be connected to an upper surface of the supporting portion 45, and may extend parallel to the upper surface of the supporting portion 45. To enable this structure, the supporting portion 45 disposed above the substrate 10 may extend higher than the previously-described supporting portions 40 of FIGS. 1A-1C, 3, and 4. The support contact portion 73c may be formed over a wide area on the upper surface of the supporting portion 45 in order to withstand the weight applied to the connection portion 70 by the thin film 50, as similarly described above with respect to the support contact portion 71a of FIG. 3. Accordingly, the weight applied to the connection portion 70 may be distributed over a wide area of the supporting portion 45 via the support contact portion 73c. The deformation portion 72c may connect the thin film contact portion 71c extending in a direction perpendicular to the thin film 50 and the support contact portion 73c extending parallel to the upper surface of the supporting portion 45. The function of the deformation portion 72c is as described above.

Figure 6A:
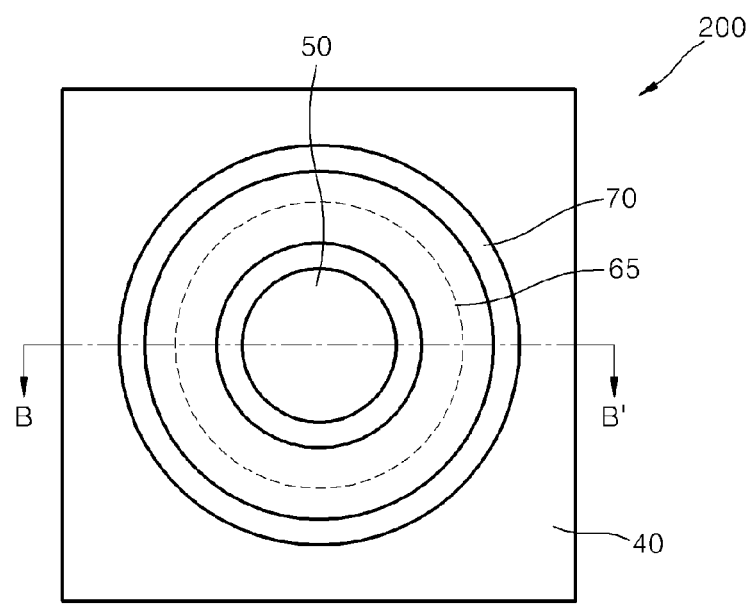
FIG. 6A is a schematic plane view illustrating a cell of an ultrasonic transducer, according to another exemplary embodiment.
Figure 6B:
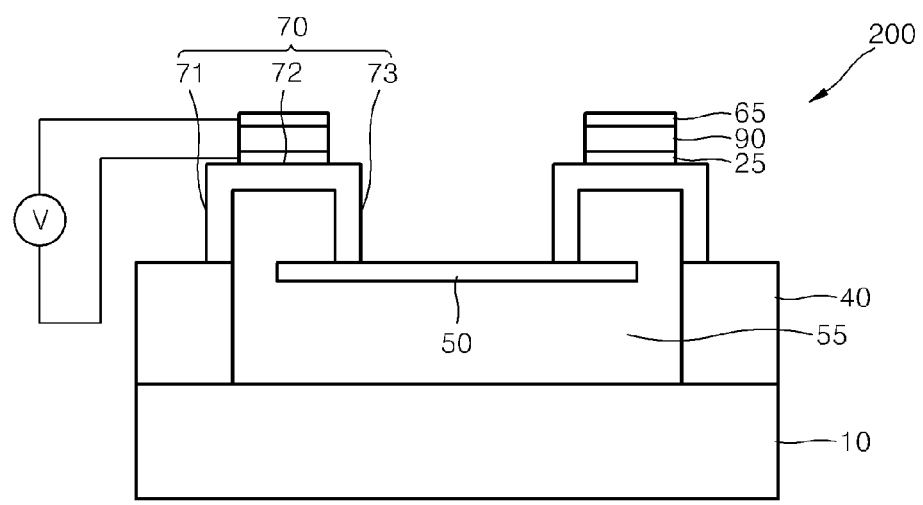
FIG. 6B is a schematic cross-sectional view of the cell of FIG. 6A.

FIG. 6A is a schematic plane view illustrating a cell 200 of an ultrasonic transducer, according to another exemplary embodiment. FIG. 6B is a schematic cross-sectional view taken along a line B-B' of FIG. 6A. Hereinafter, differences between the above-described cells 100, 110, 120, and 130 and the cell 200 respectively of FIGS. 6A and 6B will be described.

Referring to FIGS. 6A and 6B, the cell 200 may include a substrate 10, a supporting portion 40 disposed on the substrate 10, a thin film 50 spaced apart from the substrate 10 and the supporting portion 40, and a connection portion 70 for connecting the supporting portion 40 and the thin film 50. The cell 200 may further include a first electrode 25 disposed on the connection portion 70, a piezoelectric layer 90 disposed on the first electrode 25, and a second electrode 65 disposed on the piezoelectric layer 90. According to this embodiment, the cell 200 may be a cell of a pMUT. That is, the first electrode 25 and the second electrode 65 may form a piezoelectric capacitor.

The first electrode 25 may be disposed on the deformation portion 72 of the connection portion 70. The second electrode 65 may be disposed on the piezoelectric layer 90. The first and second electrodes 25 and 65 may be formed of a conductive material, for example, Cu, Al, Au, Cr, Mo, Ti, Pt, or the like. An electrical signal, for example, an AC voltage, may be transmitted from an external power source V to the first and second electrodes 25 and 65.

The piezoelectric layer 90 may be disposed on the first electrode 25, and may be formed of a piezoelectric material, for example, ZnO, AlN, lead zirconate titanate (PZT), $PbTiO_3$, La-modified $PbTiO_3$ (PLT), or the like.

When the cell 200 of the ultrasonic transducer transmits a physical signal, the piezoelectric layer 90 expands or contract in a plane direction. That is, the piezoelectric layer 90 expands or contracts in a direction parallel to the substrate 10 based on an electrical signal applied to the electrodes by an external element. An expansion force and a contraction force of the piezoelectric layer 90 causes the deformation portion 72 disposed below the piezoelectric layer 90 to be elastically deformed. When the deformation portion 72 is deformed, the thin film 50 vibrates in a direction perpendicular to the substrate 10. Accordingly, a physical signal, for example, ultrasonic waves, may be output from the cell 200 of the ultrasonic transducer.

When the cell 200 of the ultrasonic transducer according to the current embodiment receives a physical signal, the physical signal, for example, ultrasonic waves, applied by an external force may cause the thin film 50 to vibrate. When the thin film 50 vibrates, the deformation portion 72 is deformed causing the piezoelectric layer 90, disposed above the deformation portion 72, to expand or contract due to the elastic deformation of the deformation portion 72. Accordingly, the piezoelectric layer 90 may expand or contract due to an external force, and thus may generate an electrical signal due to the piezoelectric effect.

In the cell 200 of the ultrasonic transducer according to the current embodiment, the thin film 50 vibrates in a vertical direction, like a piston, with respect to the substrate 10, thereby increasing an amount of change in the volume of the cavity of the cell 200. The increase in the amount of change in a volume of the cavity may improve a transmission output and a reception sensitivity of the cell 200 of the ultrasonic transducer.

Figure 7:
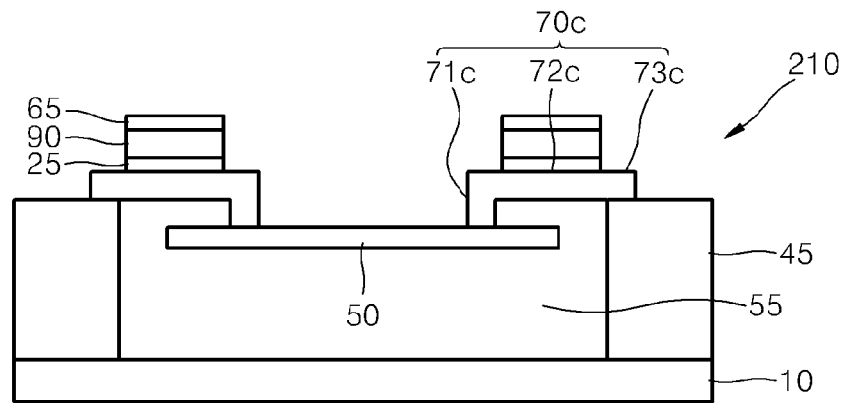
FIG. 7 is a schematic cross-sectional view illustrating a cell of an ultrasonic transducer, according to another exemplary embodiment.

FIG. 7 is a schematic cross-sectional view illustrating a cell 210 of an ultrasonic transducer, according to another exemplary embodiment. Hereinafter, differences between the above-described cells 100, 110, 120, 130, and 200 and the cell 210 of FIG. 7 will be described.

Referring to FIG. 7, the cell 210 may include a substrate 10, a supporting portion 45 disposed on the substrate 10, a thin film 50 spaced apart from the substrate 10 and the supporting portion 45, and a connection portion 70c for connecting the supporting portion 45 and the thin film 50. The cell 210 may further include a first electrode 25 disposed on the connection portion 70c, a piezoelectric layer 90 disposed on the first electrode 25, and a second electrode 65 disposed on the piezoelectric layer 90.

The connection portion 70c may connect the supporting portion 45 and the thin film 50, and may be formed of, for example, Si, $Si_xN_y$, parylene, or the like. A cross-section of the connection portion 70c may be L-shaped, as illustrated in FIG. 7. The connection portion 70c may include a thin film contact portion 71c, a support contact portion 73c, and a deformation portion 72c. The thin film contact portion 71c is connected to an upper surface of the thin film 50, and extends in a direction perpendicular to the thin film 50. Ends of the thin film contact portion 71c may be configured to increase contact areas between the ends of the thin film contact portion 71c and the thin film 50. For example, the ends of the thin film contact portion 71c may extend bilaterally, similarly to the ends of the thin film contact portion 71a of FIG. 3. Accordingly, the thin film 50 may be firmly coupled to the thin film contact portion 71c.

The support contact portion 73c may be connected to an upper surface of the supporting portion 45, and may extend to be parallel to the upper surface of the supporting portion 45.

According to this embodiment, the supporting portion 45 disposed above the substrate 10 may extend higher than the previously-described supporting portions 40 of FIGS. 1A-1C, 3, and 4. The support contact portion 73c may be formed over a wide area on the upper surface of the supporting portion 45 in order to withstand the weight applied to the connection portion 70c by the thin film 50, as similarly described above with respect to the support contact portion 71a of FIG. 3. Accordingly, any weight applied to the connection portion 70c may be evenly distributed over a wide area of the supporting portion 45 via the support contact portion 73c. The deformation portion 72c may connect the thin film contact portion 71c, extending in a direction perpendicular to the thin film 50, and the support contact portion 73c extending parallel to the upper surface of the supporting portion 45. The a function of the deformation portion 72c is as described above.

Hereinafter, a channel of an ultrasonic transducer including a plurality of cells will be described in detail.

Figure 8A:
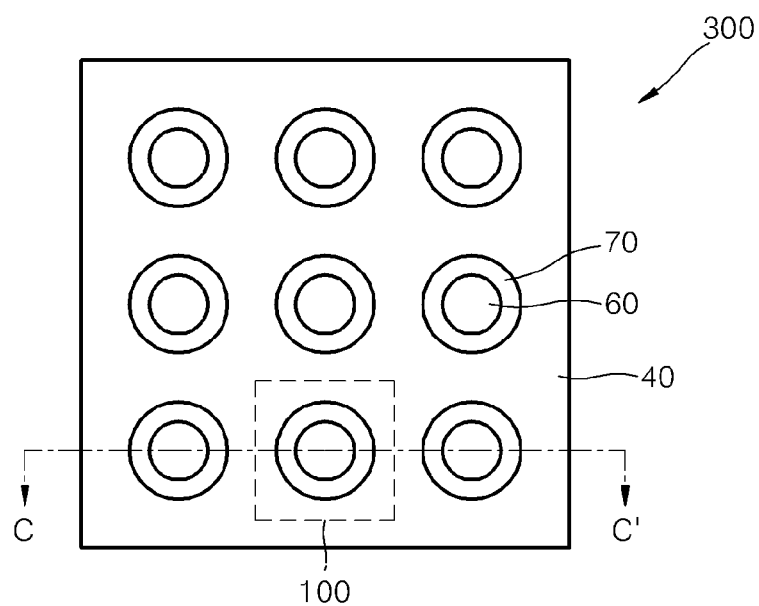
FIG. 8A is a schematic plane view illustrating a channel of an ultrasonic transducer, according to an exemplary embodiment.
Figure 8B:
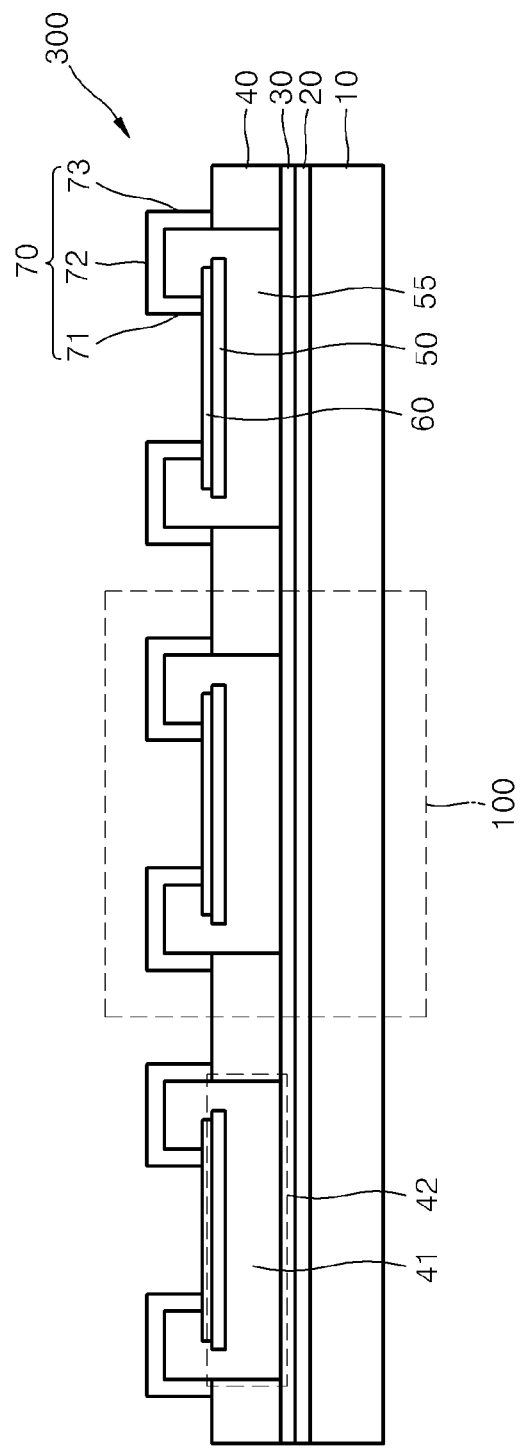
FIG. 8B is a schematic cross-sectional view of the channel of FIG. 8A.

FIG. 8A is a schematic plane view illustrating a channel 300 of an ultrasonic transducer, according to an exemplary embodiment. FIG. 8B is a schematic cross-sectional view taken along a line C-C' of FIG. 8A.

Referring to FIGS. 8A and 8B, the channel 300 includes a plurality of cells as described above. The cells 100 may be arranged in an m×n array, wherein m and n are natural numbers greater than 1. In FIG. 8A, the cells 100 are arranged in a 3×3 array. The cells 100 of the channel 300 may include one or more cells as described above with respect to cells 110, 120, 130, 200, and 210.

The channel 300 may include a substrate 10 in which recesses 41 are formed. In FIG. 8B, one of the recesses 41 is schematically shown surrounded by a dashed line 42, for illustrative purposes. A plurality of thin films 50 is disposed spaced apart from a bottom of each of the recesses 41, and a plurality of connection portions 70 each connecting one of the plurality of thin films 50 to a supporting portion 40 is formed around the corresponding recess 41. The channel 300 may further include a first electrode 20 disposed on the substrate 10 and an insulating layer 30 disposed on the first electrode 20. Each of the cells 100 may further include a second electrode 60 disposed on the thin film 50 and a feeder (not shown) connected to the second electrode 60. Each of the plurality of thin films 50, forms a cavity 55 in conjunction with a connection portion 70, the substrate 10, and the supporting portion 40. The channel 300 of the ultrasonic transducer according to the current embodiment may be a channel of a cMUT. That is, the first electrode 20 and the second electrode 60 may form a capacitor.

In the channel 300 of the ultrasonic transducer according to the current embodiment, the thin film 50 of each of the cells of the channel 300 may move in a direction perpendicular to the substrate 10, and thus an average electrostatic force and an amount of change in a volume of the cavity of each of the cells 100 (see FIG. 8B) of the ultrasonic transducer may be increased. Accordingly, a transmission output and a reception sensitivity of the channel 300 may be improved.

Alternately, instead of the first and second electrodes 20 and 60, as illustrated in FIG. 6B, one or more cells of the channel 300 may include a first electrode 25 disposed on the connection portion 70, a piezoelectric layer 90 disposed on the first electrode 25, and a second electrode 65 disposed on the piezoelectric layer 90, as described above with respect to FIG. 6B or 7. Thus, the channel 300 of the ultrasonic transducer may be a channel of a pMUT. That is, the first electrode 25 and the second electrode 65 may form a piezoelectric capacitor.

An ultrasonic transducer (not shown) according to an exemplary embodiment may include a plurality of the channels 300. A plurality of channels 300, as shown in FIG. 8B, may be arranged in an m×n array, wherein m and n are natural numbers greater than 1. As described above, the thin films 50 of the ultrasonic transducer may move in a direction perpendicular to the substrate 10, and thus an average electrostatic force and an amount of change in a volume of the cavities of the cells 100 may be increased, thereby improving a transmission output and a reception sensitivity of the ultrasonic transducer.

While exemplary embodiments have been particularly shown and described, it will be understood by those of ordinary skill in the art that various changes in form and details may be made therein without departing from the spirit and scope of the inventive concept as defined by the following claims.

What is claimed is:

1. A cell of an ultrasonic transducer, the cell comprising:
    a substrate;
    a supporting portion disposed on the substrate;
    a thin film spaced apart from the substrate and the supporting portion; and
    a connection portion which connects the supporting portion to the thin film,
    wherein the thin film extends underneath the connection portion toward the supporting portion so that an edge portion of the thin film is disposed beyond a contact point of the thin film and the connection portion.

2. The cell of claim 1, wherein the connection portion comprises:
    a support contact portion connected to the supporting portion,
    a thin film contact portion connected to the thin film at the contact point, and
    a deformation portion which connects the support contact portion and the thin film contact portion and which is elastically deformable.

3. The cell of claim 2, wherein an elastic deformation of the deformation portion causes the thin film to move in a direction perpendicular to the substrate.

4. The cell of claim 1, further comprising a first electrode disposed on the substrate.

5. The cell of claim 4, further comprising an insulating layer disposed on the first electrode.

6. The cell of claim 1, further comprising a second electrode disposed on the thin film.

7. The cell of claim 6, further comprising a feeder which is disposed on the connection portion and which is electrically connected to the second electrode.

8. The cell of claim 1, wherein the thin film comprises a conductive thin film.

9. The cell of claim 1, further comprising a piezoelectric layer disposed on the connection portion.

10. The cell of claim 9, further comprising a first electrode disposed under the piezoelectric layer and a second electrode disposed on the piezoelectric layer.

11. The cell of claim 1, further comprising a cavity defined by the substrate, the supporting portion, the thin film, and the connection portion.

12. A channel of an ultrasonic transducer, the channel comprising:
    a plurality of the cells of claim 1,
    wherein the plurality of cells are arranged in an m x n array, wherein m and n are natural numbers greater than 1.

13. The cell of claim 1, wherein the edge portion of the thin film comprises an edge which is disposed in a cavity underneath the connection portion and proximate the supporting portion.

14. A channel of an ultrasonic transducer, the channel comprising:
   a substrate comprising recesses and supporting portions;
   a plurality of thin films spaced apart from a bottom of each of the recesses; and
   a plurality of connection portions, wherein each of the connection portions connects one of the thin films to a corresponding supporting portion,
   wherein each of the plurality of thin films extends underneath a corresponding connection portion toward the corresponding supporting portion so that an edge portion of the thin film is disposed beyond a contact point of the thin film and the corresponding connection portion.

15. The channel of claim 14, wherein each of the connection portions comprises:
   a support contact portion connected to the supporting portion,
   a thin film contact portion connected to the thin film at the contact point, and
   a deformation portion which connects the support contact portion and the thin film contact portion and which is elastically deformable.

16. The channel of claim 15, wherein an elastic deformation of the deformation portion causes the thin film to move in a direction perpendicular to the substrate.

17. The channel of claim 14, further comprising a plurality of first electrodes, wherein each of the first electrodes is disposed in the bottom of one of the recesses.

18. The channel of claim 17, further comprising an insulating layer disposed on each of the first electrodes.

19. The channel of claim 14, further comprising a plurality of second electrodes,
   wherein each of the second electrodes is disposed on one of the thin films.

20. The channel of claim 19, further comprising a plurality of feeders,
   wherein each of the feeders is disposed on one of the connection portions and is electrically connected to one of the second electrodes.

21. The channel of claim 14, wherein at least one of the plurality of thin films comprises a conductive thin film.

22. The channel of claim 14, further comprising a plurality of piezoelectric layers,
   wherein each of the piezoelectric layers is disposed on one of the connection portions.

23. The channel of claim 22, further comprising a plurality of first electrodes and a plurality of second electrodes,
   wherein each of the first electrodes is disposed under the piezoelectric layers and each of the second electrodes is disposed on one of the piezoelectric layers.

24. The channel of claim 14, further comprising a plurality of cavities, each of the cavities formed in the recess and defined by the substrate, one of the supporting portions, one of the thin films, and one of the connection portions.

25. An ultrasonic transducer comprising a plurality of the channels of claim 14, wherein the channels are arranged in an m×n array, where m and n are natural numbers greater than 1.

* * * * *